United States Patent [19]

Franke

[11] 4,282,432

[45] Aug. 4, 1981

[54] X-RAY DIAGNOSTIC GENERATOR WITH AN MAS RELAY

[75] Inventor: Kurt Franke, Erlangen, Fed. Rep. of Germany

[73] Assignee: Siemens Aktiengesellschaft, Berlin & Munich, Fed. Rep. of Germany

[21] Appl. No.: 85,700

[22] Filed: Oct. 17, 1979

[30] Foreign Application Priority Data

Oct. 25, 1978 [DE] Fed. Rep. of Germany ....... 2846531

[51] Int. Cl.³ .......................... A61B 6/00; H05G 1/46

[52] U.S. Cl. .................................... 250/322; 250/402; 250/413

[58] Field of Search ................ 250/415, 402, 413, 322

[56] References Cited

U.S. PATENT DOCUMENTS

| | | | |
|---|---|---|---|
| 3,356,847 | 12/1967 | Splain | 250/413 |
| 4,160,906 | 7/1979 | Daniels et al. | 250/402 |

OTHER PUBLICATIONS

Schmitmann et al., "Tridoros Optimatic—A New Generator System," *Electromedica,* 1971, No. 3, pp. 83–86.

*Primary Examiner*—Alfred E. Smith
*Assistant Examiner*—T. N. Grigsby
*Attorney, Agent, or Firm*—Hill, Van Santen, Steadman, Chiara & Simpson

[57] ABSTRACT

In an exemplary embodiment, an mAs relay having selector keys and also a digitally operating manual control for selection of mAs products is capable of being switched over for digital selection of the exposure time independently of later radiographic current selection. For this purpose, the input of the mAs relay is capable of connection to an auxiliary current source which delivers a constant auxiliary current. The operating threshold of the mAs relay is then adjusted by the digital selection of exposure time. For the purpose of overload protection, a power circuit can be present which in a step-by-step fashion reduces the x-ray tube power via the x-ray tube current to a permissible value when preprogrammed times, e.g. planigraphic exposure times provided for planigraphic operation, are exceeded for the given settings of radiographic current and voltage.

4 Claims, 1 Drawing Figure

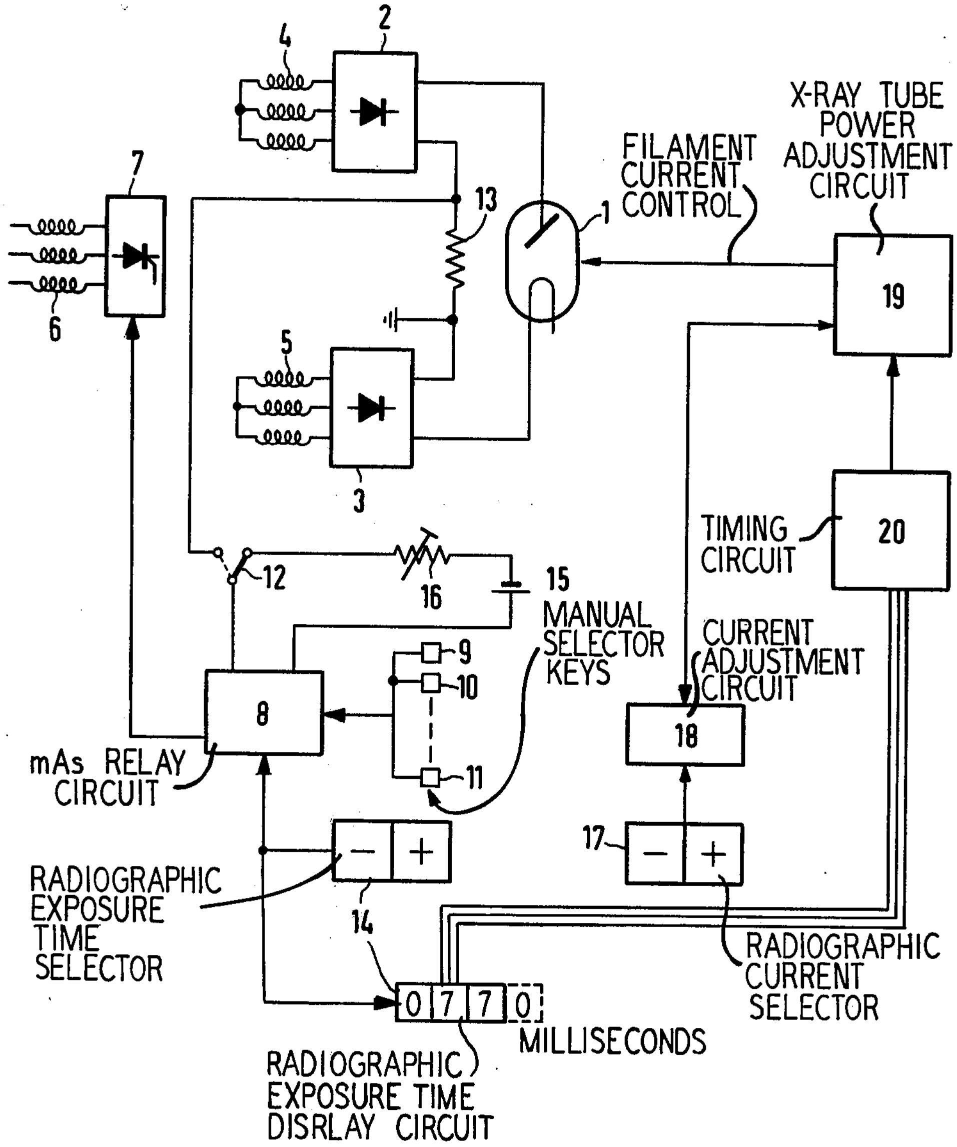
2
4
7
13
1
FILAMENT CURRENT CONTROL
X-RAY TUBE POWER ADJUSTMENT CIRCUIT
19
6
5
3
12
16
15
TIMING CIRCUIT
20
MANUAL SELECTOR KEYS
9
10
11
8
CURRENT ADJUSTMENT CIRCUIT
18
mAs RELAY CIRCUIT
17
RADIOGRAPHIC EXPOSURE TIME SELECTOR
14
RADIOGRAPHIC CURRENT SELECTOR
0 7 7 0
MILLISECONDS
RADIOGRAPHIC EXPOSURE TIME DISRLAY CIRCUIT

X-RAY DIAGNOSTIC GENERATOR WITH AN MAS RELAY

BACKGROUND OF THE INVENTION

The invention relates to an x-ray diagnostic generator with a mAs relay with which organ keys are associated for the purpose of organ-programmed selection of mAs products.

An x-ray diagnostic generator of this type is described in the publication "Electromedica" 3, 1971 on pages 83 through 86. In the case of this x-ray diagnostic generator, organ keys are provided through the actuation of which preprogrammed exposure values; among other things, the mAs product, are selectable. In addition, the possibility exists of selecting the exposure values individually. This individual selection possibility is provided, since users repeatedly express the desire for having an individual adjustment possibility. In the case of the known x-ray diagnostic generator, it is not possible to select the exposure time and the x-ray tube current separately and individually. However, also this selection possibility is in great demand.

SUMMARY OF THE INVENTION

The object underlying the invention resides in developing an x-ray diagnostic generator of the type initially cited such that, with simple means, particularly without a great additional outlay, an individual adjustment of the exposure time is possible, whereby the individual current adjustment can then proceed in a known fashion via the filament circuit of the x-ray tube.

This object is solved in accordance with the invention by virtue of the fact that, for the purpose of individual adjustment of the exposure time, the input of the mAs relay is connectable to an auxiliary current source which supplies a constant auxiliary current, and that the operating (or response) threshold of the mAs relay is adjustable through time adjustment means. In the case of the inventive x-ray diagnostic generator, the mAs relay is switched over to a time switch for the case in which an individual time adjustment takes place. The adjustment of the x-ray tube current can, in this instance, proceed by means of a known current selector via the filament circuit of the x-ray tube. The x-ray tube voltage can likewise proceed individually, in a known fashion; for example, by means of a regulating transformer which is connected to the high voltage transformer.

A further development of the invention consists in that, for the purpose of overload protection, a power adjustment circuit is present which in a step-by-step fashion reduces the x-ray tube power via the x-ray tube current to permissible values when preprogrammed times are exceeded. In this further development, a reduction of the adjusted x-ray tube current to a permissible value, if necessary, proceeds automatically in dependence upon the individual adjustment of the exposure time. The preprogrammed times, in which the power switch-over takes place, can expediently be those particular times which are provided as the planigraphic times for the utilization of the generator in conjunction with x-ray planigraphic scanning modes. Since, in the case of planigraphic operation, the exposure time is fixedly prescribed by the planigraphic scanning mode of the radiography apparatus, an automatic adjustment of the x-ray tube current, in dependence upon the respectively selected planigraphic time can proceed via the x-ray tube current selector.

The invention shall be explained in further detail in the following on the basis of an exemplary embodiment represented in the accompanying sheet of drawings; and other objects, features and advantages will be apparent from this detailed disclosure and from the appended claims.

BRIEF DESCRIPTION OF THE DRAWINGS

The single FIGURE is an electric circuit diagram showing an exemplary embodiment in accordance with the present invention.

DETAILED DESCRIPTION

In the drawing, an x-ray tube 1 is illustrated which is supplied by two series-connected high voltage rectifiers 2 and 3. The high voltage rectifiers 2 and 3 are connected to the secondary winding groups 4 and 5 of a three-phase high voltage generator whose primary winding group 6 is fed by the three-phase mains. For the purpose of switching the x-ray tube 1 on and off, there is provided, in the star point (or neutral point) of the primary circuit of the high voltage transformer 4 through 6, a three-phase current rectifier in whose d.c. current branch a switching element with an ignition characteristic is disposed. The switching circuit thus formed is referenced in the drawing by 7 and is controlled by an mAs relay 8 so as to effect the switching off of the x-ray tube 1 upon reaching a predetermined mAs product; i.e. upon exceeding a selected operating threshold for the mAs product. The mAs product is selectable, in an organ-programmed fashion, by means of organ keys of which three keys 9 through 11 are illustrated in the drawing. In the case of organ-programmed operation, a switch 12 occupies its position, indicated by broken lines, in which a signal corresponding to the x-ray tube current, tapped at a resistance 13 in the high voltage circuit, is supplied to the mAs relay and integrated there.

For the purpose of individual adjustment of the exposure time by means of a time switch 14, the mAs relay is likewise utilized. If the time selector 14 is actuated, the switch 12 is changed over into its position illustrated by the solid line. In this case, the input of the mAs relay 8 is connected to an auxiliary current source 15 which supplies a constant auxiliary current, adjustable by a resistance 16, to the mAs relay. The operating threshold of the mAs relay 8 is, in this instance, individually adjusted by the time switch 14. In this manner, it is possible to operate the mAs relay 8 as a time switch. In the case of a free adjustment of the exposure time via the time switch 14, the x-ray tube current can also be individually adjusted via a current selector 17 and a current adjustment circuit 18. The current adjusting circuit 18 effects the current adjustment via a power circuit 19. The power circuit is controlled by a timing circuit 20 to which a signal is supplied corresponding to the time individually selected by means of the time switch 14. In the timing circuit 20, predetermined times are programmed, upon the exceeding of which the x-ray tube power is reduced via the x-ray tube current to respectively permissible values. To this end, the power circuit 19 receives also information regarding the respectively adjusted x-ray tube voltage. The times in which a power reduction occurs can, in a particularly simple fashion, be those times which are provided as the planigraphic exposure times for the utilization of the generator in conjunction with x-ray planigraphy; for example, 0.2, 0.4, 0.64, 1.2, 2.5, 3.2 and 5 sec. During the planigraphic operation, wherein the exposure time is fixedly prescribed by the operating sequence mechanism of the planigraphic apparatus, the x-ray tube current must be adjusted corresponding to the selected planigraphic exposure. This adjustment likewise proceeds via the current adjusting circuit 18.

Supplemental Discussion

By way of exemplary details, the mAs relay of component 8 may correspond to that found in the six-pulse 50 kW diagnostic x-ray generator system known as TRIDOROS OPTIMATIC (see the brochure Order No. MR 50/1207.101 of March 1975, pages 16 and 17); in this system there is presently a central control console for free (non-programmed) setting of tube voltage (kV) and mAs product. In the existing equipment, in planigraphy, an automatic circuit which may form part of component 20 receives information required for automatic setting of the tube current when the desired planigraphic program and thus the exposure time has been set at the planigraphic x-ray unit. In one type of commercial planigraphic equipment known as the OPTIPLANIMAT (Siemens AG brochure Order No. MR 26/7107.101 of July 1975) the respective planigraphic programs which may be selected are as follows:

| | Planigraphic programme | | | |
|---|---|---|---|---|
| | Blurring pattern | Planigraphic angle | Planigraphic exposure time | Number of tube excursions |
| Planigraphy | Spiral | 45° | 5,0s | 5 |
| | | 45° | 3,2s | 3 |
| | | 30° | 2,5s | 3 |
| | Circular | 40° | 1,2s | |
| | | 30° | 1,2s | |
| | | 40° | 1,2s | |
| | Linear | 30° | 0,6su. 1,2s | |
| Zonography | Circular | 5° | 0,6su. 1,2s | |
| | Linear | 5° | 0,2su. 0,4s | |

For each such planigraphic program, as registered in timing circuit 20, the x-ray tube adjustment circuit 19 regulates the filament current of tube 1 to maintain a constant x-ray tube current selected by its internal programming without reference to components 14, 17 and 18, for each setting of x-ray tube voltage.

Thus, the existing commercially available part of component 19 selects constant x-ray tube current settings therein for time durations of 0.2, 0.4, 0.6, 1.2, 2.5, 3.2 and 5 seconds, for example, and for programmed x-ray tube voltage values.

It is apparent from the preceding disclosure that the capacitor and resistor values of the conventional mAs relay configuration of component 8 can be calibrated by means of variable resistor 16 so as to represent exposure time instead of mAs product. Thus if the equivalent of a constant ten milliampere current flow to the integrating circuit of relay 8 with switch 12 in the dotted line position were to result during a period of one second for a setting of mAs product of 100, the same resistor-capacitor integrating configuration as produced by such a mAs setting of 100 will give a time interval of one second if the same current of ten milliamperes is supplied by source 15, 16 with switch 12 in the solid line position shown. Accordingly, with the mAs display of the existing central console showing a selected mAs value of 100, and the resistor 16 set for a current value of ten milliamperes, the existing mAs relay configuration would be set to supply a turn-off signal to existing component 7 after a time interval of one second.

The switches 14 and 17 may be constructed in the same way as the mAs setting arrangement of the central console of the aforementioned existing commercial generator system. Thus a knob may be provided which when turned to a counterclockwise position counts the three digit decimal mAs setting down to zero, and when turned in a clockwise direction counts the mAs setting from zero up to a maximum value (such as 999 milliampere-seconds). Such manual count control and display setting means are diagrammatically represented at 14 and at 17, 18. Thus, when switch 12 is in the solid line position shown the setting controls of components 14 and 17 are active and the mAs setting control and the manual program selector keys 9–11 are disabled. In such exposure time setting mode of the central console, the actuation of the setting control of component 14 may control a digital display of the selected exposure time in suitable units such as milliseconds with counting in increments of ten milliseconds up to a maximum of 5000 milliseconds. In the specific example where a mAs setting of 100 corresponded to a time setting at component 14 of one second or one thousand milliseconds, the condition of the mAs relay 8 for a setting of ten milliseconds would correspond to an mAs setting of the existing commercial equipment of one milliampere second, so that the switching of the mAs resistance-capacitance values could be controlled by the same circuit. In other words the digital value of exposure time expressed in tens of milliseconds (e.g. 001 decimal for a ten millisecond setting) would correspond to the digital value of the mAs value expressed in milliampere-seconds (e.g. 001 decimal for a one milliampere-second setting).

Thus, as one example the counter-register of component 8 controlling the display and resistance-capacitance settings of the commercial mAs relay of component 8 can also receive the exposure time values introduced by the manual count-up, count-down selector of component 14, as indicated in the accompanying drawing by the line from component 14 which leads to component 8.

The current selector 17 and current adjustment circuit 18 may be operative with switch 12 in the solid line position in correspondence with conventional "three-button operation" (free, non-programmed selection of kV, seconds and tube current); such operation being commercially available in the modified TRIDOROS generator system known as the "TRIDOROS 5S", Siemens AG Order No. MR 62/7120.101 dated February 1976. This system offers continuously adjustable radiographic voltage from 35 kV to 125 kV, and continuously adjustable radiographic current from 20 mA to 800 mA. The maximum output values are 800 mA at 60 kV, 600 mA at 90 kV, 400 mA at 125 kV (and 50 kW at 100 kV in accordance with DIN 6822).

The TRIODOROS 5S system is provided with automatic overload protection combined with selectable limitation of load via computing system. In three button operation the seconds of exposure time, mA and kV values are freely selectable below the maximum permissible tube loading, the resultant degree of tube loading being displayed as a percentage of the maximum loading.

In the conventional three button mode, the display pointer covers both the analog mAs scale (1 to 1000)

and an analog exposure time scale in seconds (0.01 to 5 seconds), the mAs knob setting the mAs relay but the display showing the quotient of the mAs setting and the mA setting.

Thus, when modifying the TRIODOROS 5S system according to the present invention, a switch 12 is provided enabling a different mode of three button operation where the exposure time is displayed by means of three decimal digits in tens of milliseconds and the count-up, count-down control of component 14 sets a digital counter of the mAs relay of component 8. Thus the time display is entirely independent of the radiographic current value selected at 17, 18. For example, the selected exposure time value does not change when the count-up, count-down control of component 17 is actuated to select a new radiological current value. Thus with the illustrated circuit, the selectors 14 and 17 are decoupled and the selector 17 can be manipulated while the selected exposure time remains unchanged.

It will be apparent that many modifications and variations may be effected without departing from the scope of the novel concepts and teachings of the present invention.

I claim as my invention:

1. An x-ray diagnostic generator comprising a mAs relay having organ keys for the organ-programmed selection of mAs products, characterized in that, for the purpose of individual adjustment of the exposure time, said mAs relay has an auxiliary current source (15), and an exposure time selector means (14), the input of the mAs relay (8) being capable of connection to said auxiliary current source (15) to receive a constant auxiliary current independent of radiological current, such that the operating threshold of the mAs relay (8) is adjustable by the exposure time selector means (14) to provide any exposure time selected thereby.

2. An x-ray diagnostic generator according to claim 1, characterized in that the auxiliary current supplied to the mAs relay (8) by the auxiliary current source (15) is adjustable by adjustment means (16).

3. An x-ray diagnostic generator according to claim 1, characterized in that, for the purpose of overload protection, a power circuit (19) is present which in a step-by-step fashion reduces the x-ray tube power via the x-ray tube current to permissible values when preprogrammed times are exceeded.

4. An x-ray diagnostic generator according to claim 3, characterized in that the preprogrammed times in which the power switch-over takes place are those times which are provided as planigraphic times for the utilization of the generator in conjunction with an x-ray planigraphic operation.

* * * * *